United States Patent [19]
Douglas

[11] Patent Number: 6,009,632
[45] Date of Patent: Jan. 4, 2000

[54] ALIGNMENT SYSTEM FOR OPTICAL ANALYTE TESTING METER COMPONENTS

[75] Inventor: Joel S. Douglas, Los Altos Hills, Calif.

[73] Assignee: Mercury Diagnostics, Inc., Scotts Valley, Calif.

[21] Appl. No.: 08/990,084

[22] Filed: Dec. 12, 1997

[51] Int. Cl.⁷ .............................. G01N 21/00; G01B 3/14
[52] U.S. Cl. .......................... 33/562; 33/613; 422/82.05
[58] Field of Search ............................ 33/533, 562, 613, 33/645; 29/832, 833; 422/82.05

[56] References Cited

U.S. PATENT DOCUMENTS

| | | |
|---|---|---|
| 4,637,403 | 1/1987 | Garcia et al. . |
| 4,802,284 | 2/1989 | Jackson ..................................... 33/562 |
| 4,882,846 | 11/1989 | Reed ........................................ 33/562 |
| 4,994,167 | 2/1991 | Shults et al. . |
| 5,037,614 | 8/1991 | Makita et al. ....................... 422/82.05 |
| 5,053,199 | 10/1991 | Keiser et al. . |
| 5,199,182 | 4/1993 | Fowler ..................................... 33/645 |
| 5,279,294 | 1/1994 | Anderson et al. . |
| 5,281,395 | 1/1994 | Markart et al. ..................... 422/82.05 |
| 5,304,468 | 4/1994 | Phillips et al. . |
| 5,424,035 | 6/1995 | Hones et al. ............................. 422/55 |
| 5,515,170 | 5/1996 | Matzinger et al. . |
| 5,522,255 | 6/1996 | Neel et al. . |
| 5,580,794 | 12/1996 | Allen et al. . |
| 5,763,262 | 6/1998 | Wong et al. ........................... 422/68.1 |
| 5,795,543 | 8/1998 | Poto et al. ........................... 422/82.05 |
| 5,829,124 | 11/1998 | Kresge et al. ............................ 29/832 |
| 5,872,713 | 2/1999 | Douglas et al. .................... 422/82.01 |
| 5,912,134 | 6/1999 | Shartle ..................................... 422/55 |

FOREIGN PATENT DOCUMENTS

| | | |
|---|---|---|
| 0 383 209 A1 | 8/1990 | European Pat. Off. . |
| 0 351 891 | 9/1993 | European Pat. Off. . |
| WO 92/15861 | 9/1992 | WIPO . |
| WO 97/46868 | 12/1997 | WIPO . |

Primary Examiner—Christopher W. Fulton
Assistant Examiner—Quyen Doan
Attorney, Agent, or Firm—Burns Doane Swecker & Mathis L.L.P.

[57] ABSTRACT

An analyte testing meter is provided with a template for facilitating assembly during the manufacturing process. The template aligns the electro-optics components on the printed circuit board and aligns the optics block containing light directing elements such as lenses, waveguides and beamsplitters with the electro-optics elements. Other alignment features are provided which improve precision of the assembled product and obviate the need for expensive alignment equipment.

30 Claims, 6 Drawing Sheets

FIG_1

FIG_1A

FIG_2

FIG_3

FIG_4

FIG_4A

FIG_5

FIG_7

FIG_6

FIG_6A

ALIGNMENT SYSTEM FOR OPTICAL ANALYTE TESTING METER COMPONENTS

BACKGROUND OF THE INVENTION

1. Field of the Invention

The present invention relates to analyte testing devices, and more particularly, to an alignment system for an optical analyte testing device.

2. Description of Related Art

The need for simple methods to determine the chemical and biological constituents in bodily fluids has increased as point of care testing has gained in popularity. The most common application is the self-monitoring of blood glucose concentrations by patients with diabetes. Diabetic patients frequently administer insulin or take other therapeutic actions based on the test results. As testing is generally recommended multiple times daily and may occur in any setting, an easy to use and relatively inexpensive method to accomplish this task is required. The costs of testing are significant to many diabetic patients, especially elderly patients with fixed incomes and those who are not reimbursed by health insurance plans.

In addition to chronic disease monitoring, there are other applications where simple, low cost testing at the point of care may be desired. For example, many practitioners believe that certain medications could be administered much more effectively, both from a medical outcomes and from a cost perspective, if the circulating level of such medications could be monitored during the course of treatment. Generally, if the level of an analyte or biological agent is important enough, the patient needs to go to a clinic or laboratory and submit to a venipuncture so a test may be run on an expensive clinical instrument. The ability to inexpensively monitor the patient either in the doctor's office or at home could lead to improved outcomes. Given the current pressures on improving the cost effectiveness of health care, inexpensive, easy to use alternatives to expensive test methods would be welcomed.

The National Institutes of Health conducted a large scale study to evaluate the benefit of long term tight control of the blood glucose for the diabetic patient. The study, known as the DCCT, proved that long term tight control of the blood glucose levels in patients had a direct relationship to the health of the patient. One way for the medical profession to monitor the condition of a patient is for the patient to use a blood glucose monitoring system which has a memory unit to record the blood glucose level and other data such as date and time.

Systems for monitoring a patient's condition operate by measuring the concentration of an analyte in a bodily fluid sample derived from the patient. The bodily fluid may include blood, interstitial fluid, or urine. The sample is applied to a portion of a disposable test strip having impregnated therein a reagent selected to react with the particular analyte being tested. The reaction is manifested by a physically detectable change, such as an electrical conductivity increase or a change in an optical property, which is in proportion with the concentration of the analyte in the sample.

The physical change in the test strip is measured using known electrical, electro-optical, electro-chemical or other techniques. The measurement is implemented with appropriate circuitry and/or optics disposed in a meter provided separately from the test strip. The meter engages the test strip such that the physical change caused by the reaction of the analyte with the reagent can be measured by the meter, which then processes the information and generates an indication signal proportional to the concentration of the analyte in the sample.

The alignment of the optical components is important because shifts in the orthogonal coordinates x, y or z result in substantial changes in the reflected light being focused on the detection surface of the photodetector. If the amount of light reflected changed then the results of the test can be compromised. To accomplish the alignment of the components of the prior art meters, an electronic printed circuit board (PCB) is fabricated using precision pick and place equipment which can place the components within 0.0005 inches of true position. The optics block is then located to the component placement by precision holes drilled in the PCB or by a fixture which locates the optics block in relationship to the electronic components. The optics block can assume different configurations which achieve a variety of purposes. One configuration has a series of lenses which transport the light from the LED to the photodetector. A second provides a light piping mechanism similar to fiber optics to transport the light, and a third method creates light tubes which channel the light within the optics block. Any alternate design for the optics light transport system which could be envisioned will work with this method and one skilled in the art could conceive of an alternative means. Lensed optics systems have been used in security systems (i.e. fingerprint recognition) and single uses medical meters but the alignment of the components has required considerable effort to insure proper integration into the test systems.

Many diabetics currently use a test method described in U.S. Pat. No. 5,304,468 to Phillips et al. This system is comprised of an electronic meter and a disposable test strip. The meter reads the color change of the strip, the color change correlating to the concentration of the analyte in the sample applied to the strip. The meter is an expensive and complex instrument which uses multiple light sources or detectors to isolate the reagent color change from the sample color. The user must select the calibration code for the meter to match the calibration code of the test strips. In this way, the meter accommodates a wide range of test strip performance values. The system's optics are large and expensive to manufacture due to the precision alignment requirements of the detector and light source.

U.S. Pat. No. 4,637,403 to Garcia et al. describes an integrated system which provides a method by which the patient lances the finger to get a sample of blood which is then used by the device to read the quantity of analyte in the sample. This system uses a complex optical reflectance system to read the analyte level in the sample.

U.S. Pat. No. 5,279,294 to Anderson et al. describes a hand held shirt pocket device for quantitative measurement of glucose or analytes in biological fluids. The device has a sophisticated electronics system and a sampling system integrated into one device to determine the quantity of analyte in a bodily fluid sample.

U.S. Pat. No. 5,515,170 to Matzinger et al. describes the difficulties of keeping a strip holder and optics system clean and the need to present the test strip in the proper perspective to the optics.

European Patent Specification 0 351 891 B1 to Hill et al. describes an electro-chemical system and electrodes which are suitable for the in vitro determination of blood glucose levels. The system requires the use of expensive electrodes and a sophisticated reader to determine blood glucose levels.

U.S. Pat. No. 4,994,167 to Shults et al. describes a measuring device for determining the presence and amount of a substance in a biological fluid using electro-chemical methods. This system requires a complex instrument and method for the patient to determine the quantitative result.

U.S. Pat. No. 5,580,794 to Allen et al. describes a single use disposable measuring device for determining the presence and amount of a substance in a biological fluid using reflectance methods. This system utilizes an optics and electronics package which are mated in a single plane.

U.S. Pat. No. 5,522,255 to Neel et. al. describes a fluid dose, flow and coagulation sensor for a medical instrument which uses a non-volatile electronic calibration device in the system to check the calibration of the reagent strip.

U.S. Pat. No. 5,053,199 to Keiser et. al. describes an electronically readable information carrier for use with a medical device.

Although many improvements have been made, the cost and complexity of measuring analyte levels in biological samples remains a significant issue for patients and for the health care system. Even patients who are covered for blood glucose monitoring supplies must often purchase the meter and await reimbursement. The need to construct expensive optical systems adds cost and complexity for the manufacturers. The cost of the optics systems is a significant cost of the diagnostic meter and simplifying and reducing this cost factor can have a significant affect on the price to the consumer. The availability of a low cost, simplified quantitative test system for the periodic monitoring of constituents of biological fluids, such as glucose in blood, would make testing more accessible to patients and would improve their well-being and reduce the cost of their care.

SUMMARY OF THE INVENTION

An advantageous feature in accordance with the invention is the provision of a method and apparatus for assembling a low cost optics system using simple tools and systems to reduce the cost and improve the accuracy of an optical based diagnostic system.

Another advantageous feature in accordance with the invention is the provision of a method and apparatus by which the reagent test strips can be accurately mounted into the meter to reduce the need to compensate for inaccuracy in alignment by the test strip. This will make the actual test spot used by the meter smaller which will reduce the cost of the strip and meter. Integration of the optical system with the test strip holder provides a method by which the reagent test strips can be accurately mounted into the meter to reduce the need to compensate for inaccuracy in alignment by the test strip. This will make the actual test spot used by the meter smaller which will reduce the cost of the strip and meter.

Still yet another advantageous feature in accordance with the invention is the elimination of the need for a separate test strip holder, simplifying the interface of the disposable test strip with the meter.

An embodiment in accordance with the invention involves the development of a low cost meter which uses low cost electronics and optics to create a system which is capable of self aligning the electronics, LED and photodetector (PD), to an optics system which transmits and focuses the light emitted by the LED so that it reflects off of the test strip and is focused onto the photodetector. The electronics used are simple and low cost to help achieve this goal. One method which can be used to accomplish this is to use unpackaged semiconductor based LEDs and photodetectors to build the sensing system. These components are accurately placed and aligned to the optics block which provides a light path for the emitted light from the LED and the reflected light from the strip to the photodetector from the test strip. This insures that the light emitted from the LED is not transmitted to a non-functioning part of the strip or intersects the associated aperture.

The invention eliminates the costly and time consuming prior art alignment techniques and achieves high alignment and precision by using various advantageous features. One feature is the use of a base template which may have positioning features for the electronic components, LEDs and PDs. The template may also have alignment features for positioning the optics block with the electronics. To accomplish this part of the invention the template is made having the necessary alignment features built into it. The template itself can be either injection molded or formed by die cutting. Liquid Crystalline Polymer (LCP) is an ideal material for this molding operation due to its heat stability although other materials may also be used. A third feature of the invention may be the use of locating features built into the optics block which form part of the strip holder and assist in the accurate locating of the strip. The strip holder, which also acts as a shield to control light communication between the strip and the meter and to limit the effects of ambient light on the measurement, is aligned with the optics block using an alignment feature provided on the optics block which interlocks the shield/strip holder and provides a locating feature for the strip. The shield/strip holder thus serves two functions. The first is to align the strip to the optics block. It provides the additional features needed to align and hold the strip to the optics block main pin. The second function is to provide an aperture and seal the ambient light from the optics assembly when it is installed in a meter housing. In this manner, the invention eliminates the need to accurately align the various components during manufacturing because the system is self-aligning. It uses the base template to locate the electronics components and the test strip via the optics block.

The preferred embodiment of the meter incorporates a molded lens optic system consisting of one or more channels and a simple electronics package consisting of light emitting diodes (LEDs), analog to digital conversion electronics, a processor unit, Read Only Memory (ROM), Random Access Memory (RAM) and a digital display system. The optics system and meter incorporates a positioning system which interfaces with the test strip and electronics to create positive location and alignment for the reagent test pad within the strip and the optics.

An attendant advantage to the invention is the simplification of the assembly of the device during manufacture. This allows the manufacture to eliminate the expensive assembly equipment to guaranty alignment and eliminates the tolerance stack up errors by using the optics template to align all the optics components, optics block, electronic components, shield/strip holder and strip. This is accomplished by using the features in the optics template to align all the components. The strip alignment is a reference alignment with respect to the optics template because the shield/strip holder may be aligned to the electronics components through a locating pin for the strip in the optics block. The reagent test strip may have features which mate with the optics block pin protruding through the shied/strip holder and a keyway which is designed to accept an alignment pin molded into the test strip.

The invention provides improvements over existing technology in use today in several ways. The preferred embodiment of the invention eliminates the need for a manufacture to purchase expensive equipment to accurately pick and place the electronic optics components (die) with respect to the artwork of the printed circuit board and it eliminates the need to precision drill the alignment holes for the optics block. It also eliminates the existing dependence on the positioning of the test strip holder to the optics due to integrating the optics block reference feature into the strip holder. This permits the system to be aligned to a much closer tolerance. An additional advantage of the invention is repeatability. By using injection molded parts, the tolerances can be held more closely and the repeatable assembly of the components is consistent. If the material used to mold the part is stable and the die remains in good condition then the parts molded will be of consistent quality and stable feature dimensions which insures repeatability. This reduced cost manufacturing method provides benefits to the customer in that the product cost is reduced which can be passed onto the customer. The invention provides a simple system for measuring analytes such as glucose by incorporating advanced lens-based optics and low cost modern electronics. The use of lens based optics permits the system to focus on small reaction area which reduces the size of the test pad. This enhances the invention because the variation of offsets of the components is reduced which means that a smaller spot size can be utilized which has the affect of smaller sample size being required by the test strip to guaranty test spot coverage. The resulting small test pad reduces the cost of the matrix employed and the quantity need of expensive reagents and membrane needed to conduct an accurate assay. An added benefit is that with a smaller test pad, a smaller sample volume is adequate.

In the preferred embodiment the optics system uses lenses to focus the light emitted from the LED onto the test pad and to focus the reflected light from the test pad onto a detector. The system conserves the energy used and minimizes the amount of light required by the system to determine the color change. The optics modules may be calibrated during the manufacture of the meters. By guaranteeing a consistent alignment the calibration of the meter is far more stable than a device made from components with a wider tolerance stack up due to placement errors.

In operation, a device in accordance with the invention is used by applying the sample to be tested to the reagent test strip. The applied sample, which may be bodily fluid or other analyte-containing sample, reacts with the reagents impregnated in the test pad within the test strip and the resulting color change is read by the optics and electronics systems. The signal is converted and displayed on the digital readout and/or stored in memory as the concentration of the analyte in the sample. This measured concentration may also be downloaded to a remote site, such as an internet location or electronic bulletin board, for processing and analysis at a different location.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENTS

Figure 1:
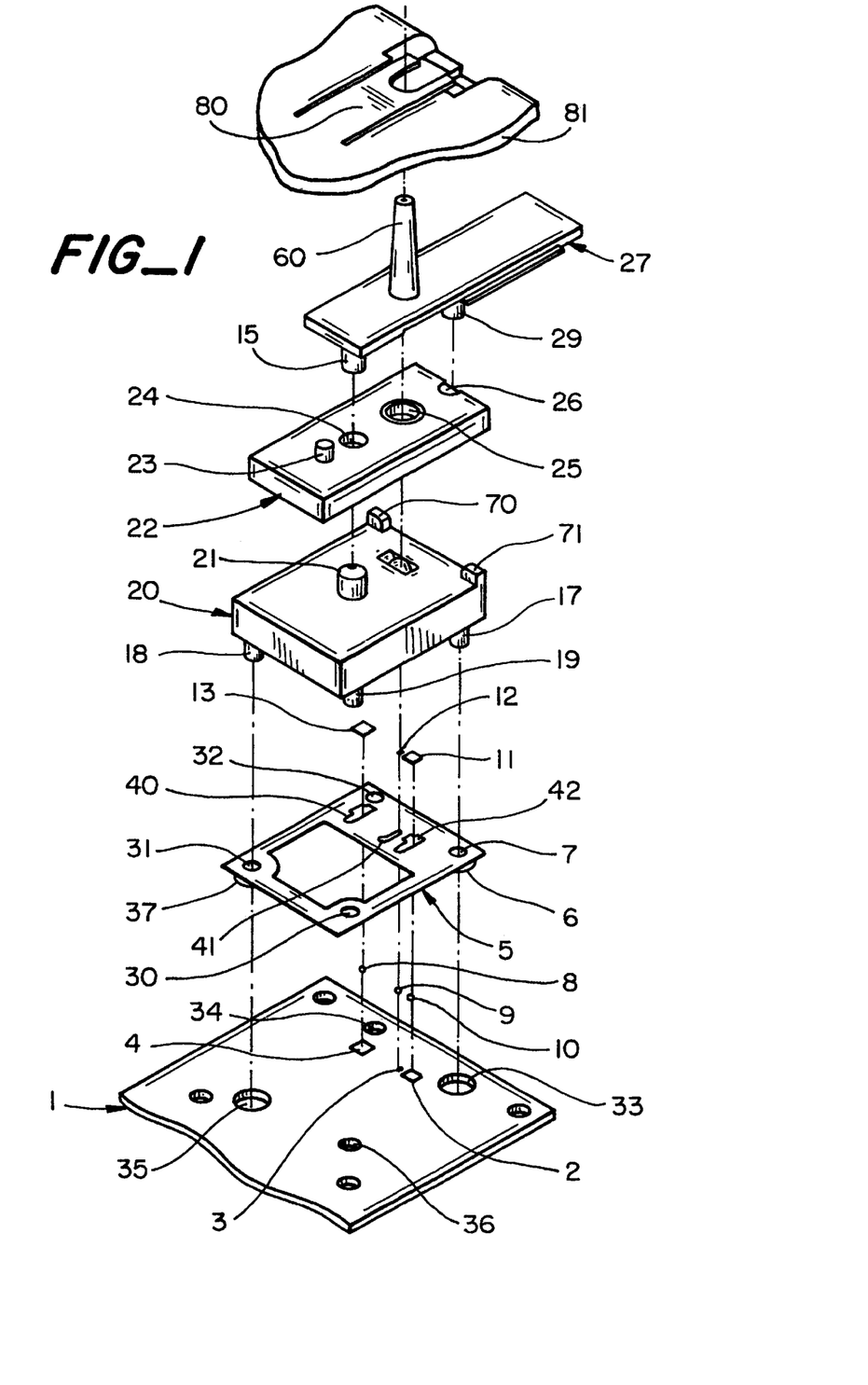
FIG. 1 is an exploded perspective view of the optical system in accordance with the invention.
Figure 1A:
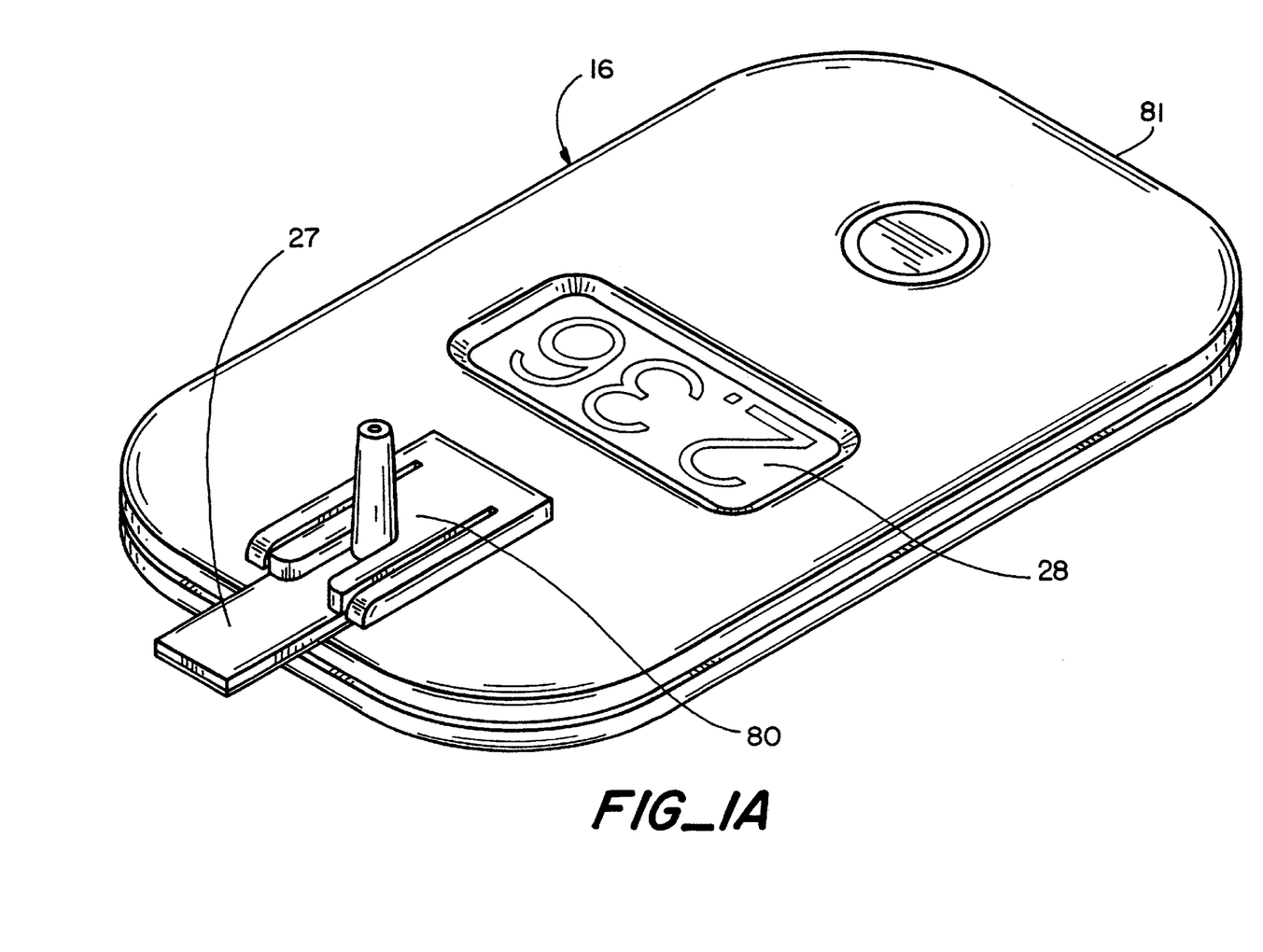
FIG. 1A is a perspective view of the meter of the invention in communication with a test strip during a measurement operation.
Figure 2:
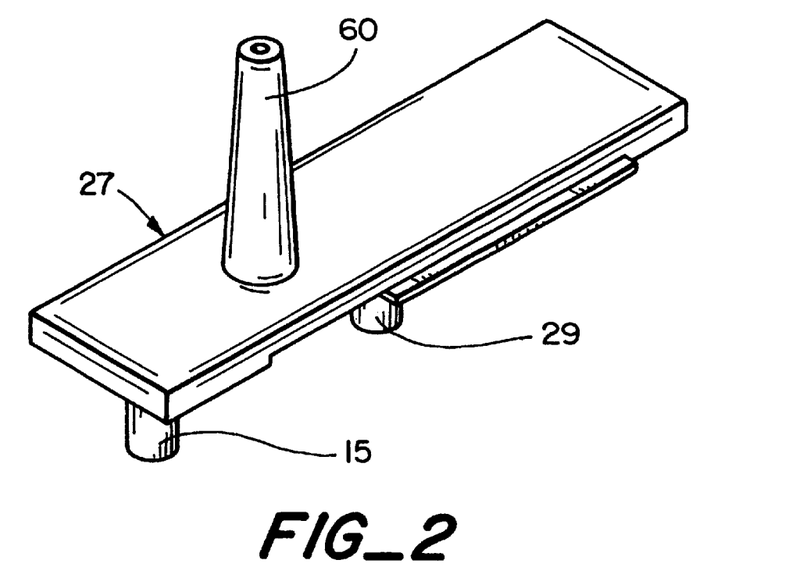
FIG. 2 is a perspective view of strip of FIG. 1.

FIG. 1A shows a meter 16 in communication with a reagent test strip 27. The test strip 27, which carries a sample-reagent reaction for observation and analysis by the meter, is positioned such that the optics components of the meter 16 are able to observe the reaction to yield an indication of the analyte concentration. As shown in FIG. 2, the test strip 27 is provided with a capillary tube 60 to conduct the fluid sample containing the analyte to the test pad (not shown) within the strip 27 and on which the reagent is disposed. The meter 16 is equipped with a meter case cover 81 and a display 28 for providing a visual indication of the measurement result. Spring tab 80 operates to engage test strip 27 and retain it in proper alignment for accurate measurement.

FIG. 1 shows the internal arrangement of the meter 16 in accordance with the invention. Although in the preferred embodiment shown in FIG. 1 use is made of a single emitter and two photodetectors, it is to be understood that the teachings of the invention may be practiced with other optical arrangements without departure from the spirit and scope of the invention.

As shown in FIG. 1, the meter 16 comprises PCB (Printed Circuit Board) 1 with optics template 5, optics block 20, and strip holder 22 stacked thereon. These components are all contained within meter case cover 81, which is further provided with a strip tab 80 designed to retain test strip 27 against the strip holder 22 and in optical alignment with optics block 20.

Figure 4:
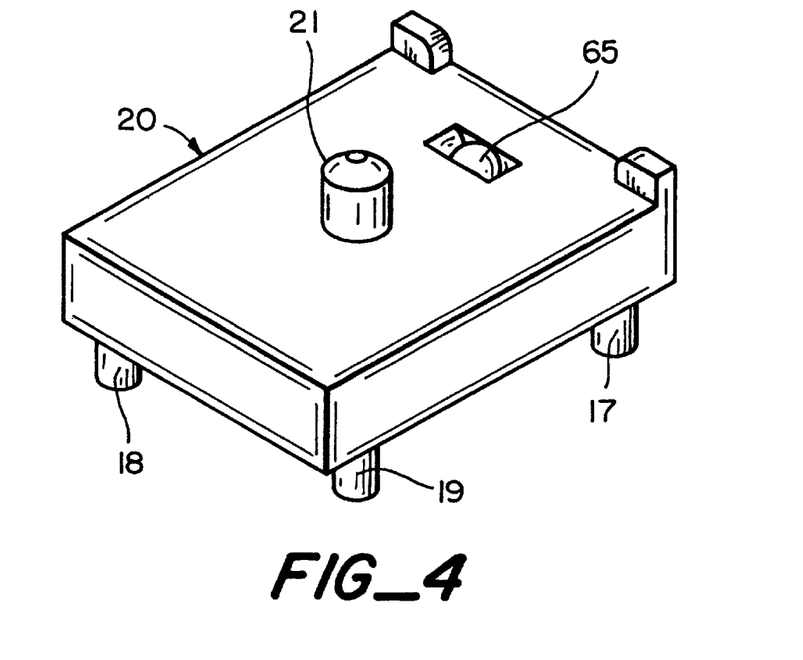
FIG. 4 is a perspective view of optics block of FIG. 1.
Figure 4A:
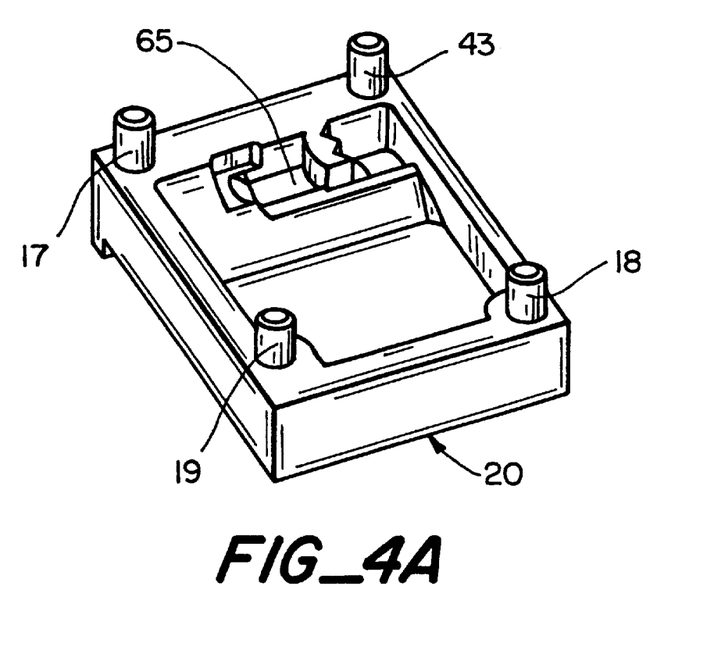
FIG. 4A is a perspective bottom view of the optics block FIG. 1.

Optics block 20 may comprise a molded plastic having light shaping or directing portions formed thereon, which may include any combination of lenses, waveguides and beamsplitters. Specifically, as shown in FIGS. 4 and 4A, a lens system 65 is disposed in optics block 20 and operates to direct light from light-emitting diode (LED) 12 onto the sample-containing portion of strip 27, and to direct light reflected from the sample-containing portion back to photodetectors 11 and 13. Various optical elements may comprise lens system 65, including but not limited to beam splitters, waveguides, and various types of light-shaping and focusing devices. The particular optics block configuration selected may depend on the type of measurements being performed, and the invention also contemplates the use of various combinations of light sources and detectors, along with measurement of colorometric, transmissive and reflective properties of the sample-reagent reaction. The ordinarily skilled artisan will be able to appropriately configure and modify the optics block 20 without patentable departure from the teachings of the invention.

Figure 3:
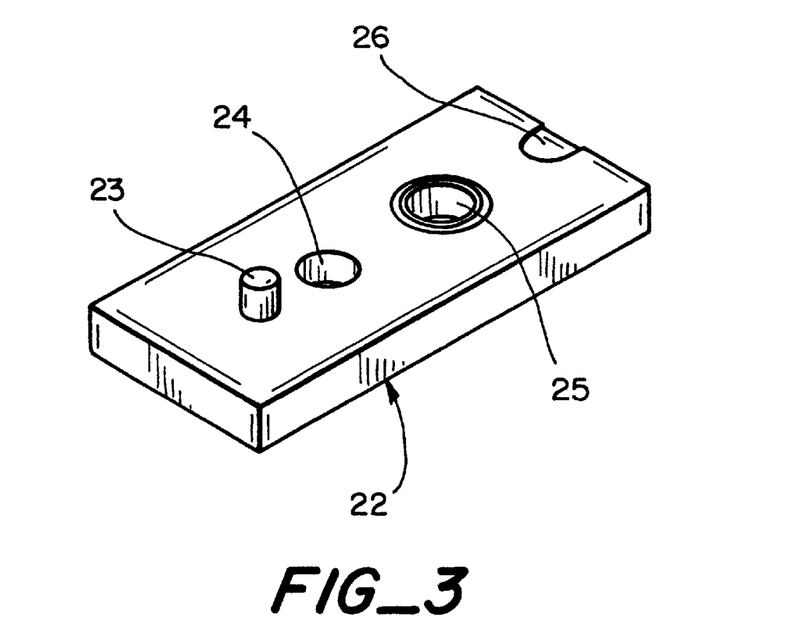
FIG. 3 is a perspective view of shield/strip holder of FIG. 1.

FIG. 3 shows in detail strip holder 22, which also operates as a light shield to optically control light communication between meter 16 and test strip 27. Specifically, light communication between these two elements is constrained to light transmissive aperture 25 formed in strip holder 22, with the rest of strip holder 22 being formed of an opaque material for blocking ambient radiation which would otherwise corrupt the light measurement process. In this manner, energy expenditure is minimized, as the aperture, in conjunction with the precisely aligned optics block, makes very efficient use of the light generated by the LED 12 and collected by photodetectors 11 and 13. Sample amounts required to make a proper measurement are similarly minimized, reducing the amount of reagent needed and overall cost of the system.

Figure 5:
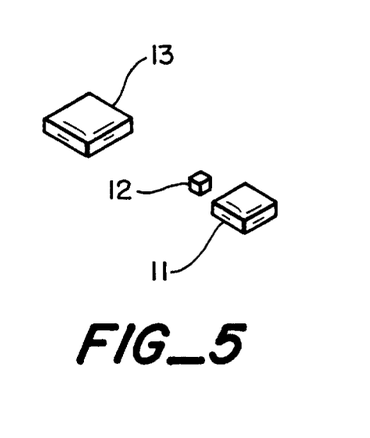
FIG. 5 is a perspective view of the optics components of FIG. 1.

The arrangement in accordance with the invention simplifies assembly of the meter 16 during the manufacturing process. The PCB 1 is provided with contact pads 2, 3, 4 for engaging the electro-optics components 11, 13, 12, which are, respectively, a pair of photodetectors and an LED. (See FIG. 5) The contact pads may be slightly larger— 0.005–0.040 larger—than the electro-optics components 11, 12, 13 in order to facilitate assembly by compensating for normal tolerance stack ups, but other configurations can be used. The PCB 1 has locating holes 33, 34, 35, 36 drilled or punched with respect to the PCB artwork (not shown). The holes are sized to accept one or more locating bosses 6, 37 formed in the optics template 5.

Figure 6:
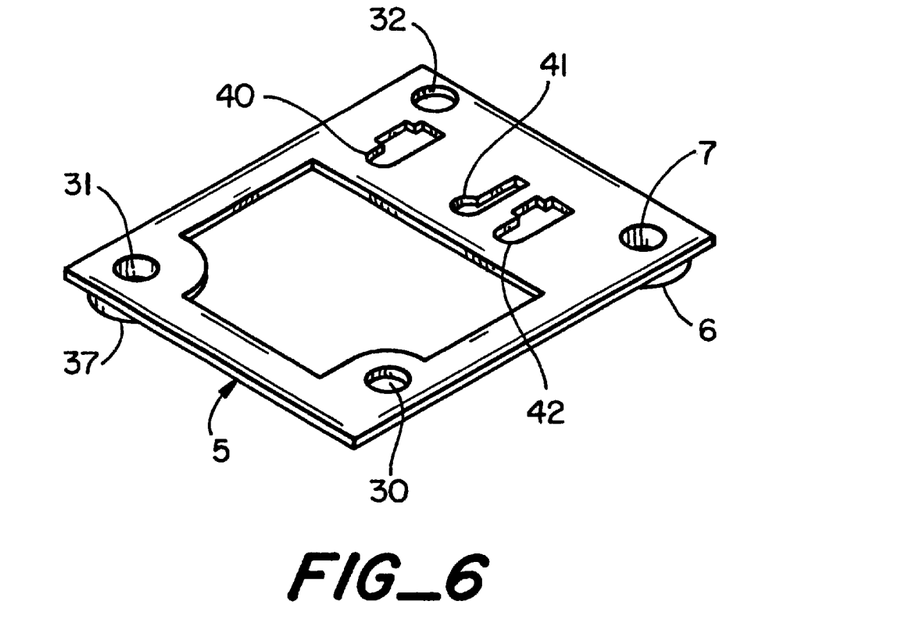
FIG. 6 is a perspective view of the optics template of FIG. 1.
Figure 6A:
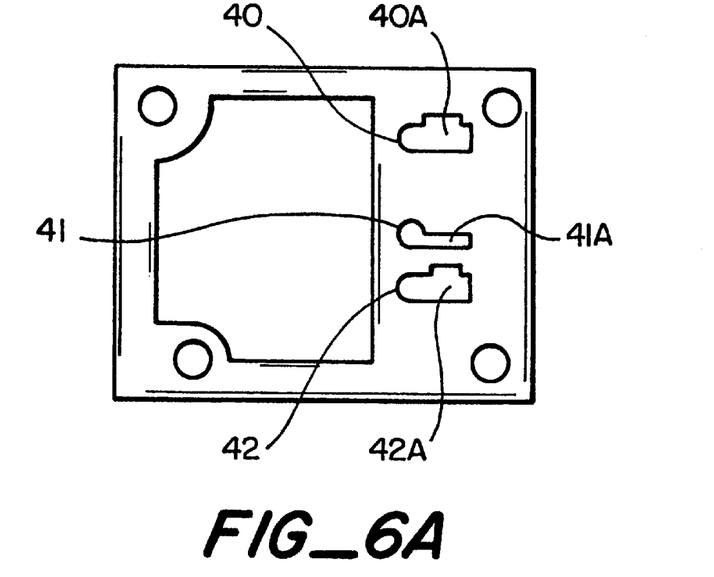
FIG. 6A is a top view of the optics template FIG. 1, showing LED and photodetectors alignment slots.
Figure 7:
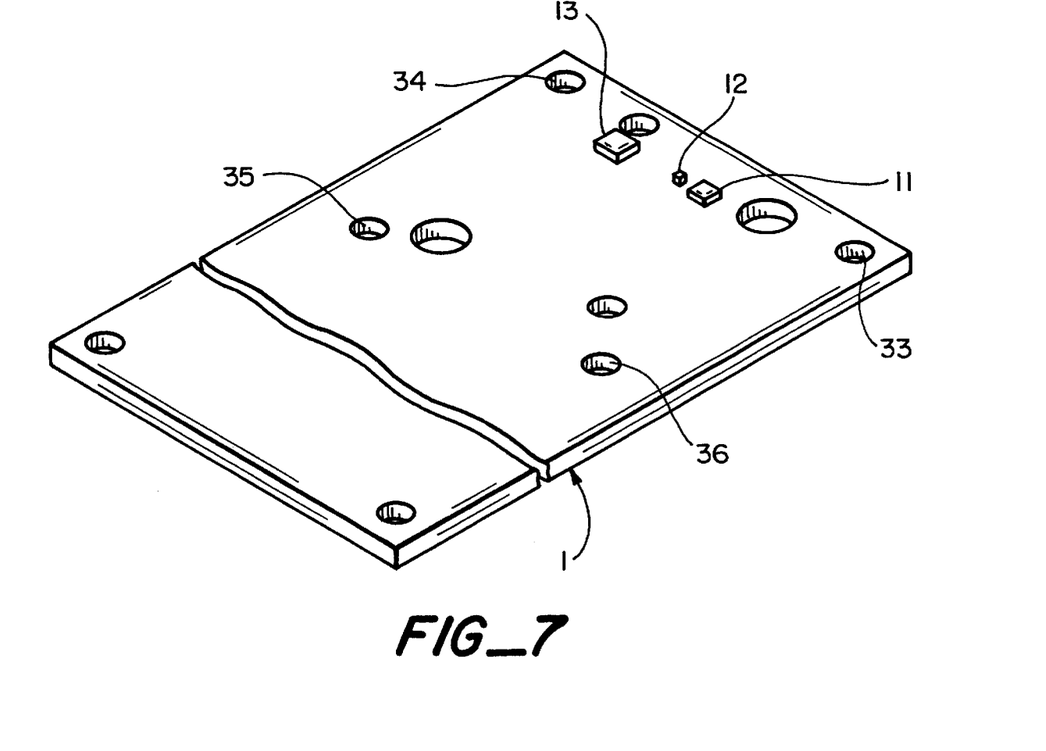
FIG. 7 is a perspective view of the printed circuit board of FIG. 1.

Assembly may be effected using portions of conductive adhesive 8, 9, 10 applied to the contact pads 2, 3, 4. Optics template 5 is placed on PCB 1 so that the locating bosses 6 and 37 fit into the PCB holes 33, 35 and may be glued in place. The bosses may be provided on either the template or the PCB, while corresponding holes are provided on the other. The electro-optics components 11, 12, 13 may be manually placed on the board through the optics template 5 as the guide. The operator may place components 11, 12, 13 through the cut-out portions, or alignment holes, 40, 41, 42. As shown in FIG. 6, these alignment holes comprise pocket portions 40A, 41A, 42A and non-pocket portions, with assembly involving sliding the electro-optics components, in the plane of the template 5, from the non-pocket portions into the pocket portions 40A, 41A, 42A. The conductive adhesive portions 8–10 are cured prior to placing the optics block 20 onto optics template 5. Curing is to the adhesive supplier's specifications but a temperature of 140 degrees Fahrenheit maintained for one hour is typical. The optics block alignment pins 17, 18, 19, 43, seen in FIG. 4A, are aligned with holes 30, 31, 32, 7 in optics template 5. The pins 17, 18, 19, 43 pass through the optics template 5 and PCB 1 holes 33, 34, 35, 36 and the pins are heat staked to the PCB 5 to hold the assembly of PCB 1, optics template 5 and optics block 20 tightly together.

Pin 21 on optics block 20 is used to align shield/strip holder 22 such that pin 21 fits at least partially into hole 24 in shield/strip holder 22. Hole 24, along with pin 23 and keyway 26, forms part of a strip engaging portion of strip holder 22 as explained below. The shield/strip holder 22 is prevented from rotating by, e.g., locking tabs 70 and 71. This forms a strip holder which can receive a strip 27 configured to fit into the system. Test strip 27 slides into the strip holder 22, being pushed into the pin 23 which forms a stop. The strip 27 rides up over the pin 21 of the optics block 20, protruding through hole 24 in shield/strip holder 22 until socket 15 mates with pin 21. Strip keyway pin 29, which is part of test strip 27, slides into keyway 26 in strip holder 22, positively locating strip 27 and preventing it from rotating in the strip holder 22. Test strip 27 is captured by spring tab 80, which may be resilient, and which is formed in the meter housing or case cover 81, with the tab 80 surrounding capillary tube 60 when test strip 27 is in place. In this manner, lens system 65, shown on FIG. 4A, is aligned to electro-optics components (11, 12, 13) and strip 27 and the LED 12 and photodetectors 11 and 13 are in optical communication with the reaction site on the test strip 27.

The above are exemplary modes of carrying out the invention and are not intended to be limiting. It will be apparent to those skilled in the art that modifications thereto, including, e.g., other alignment features, can be made without departure from the spirit and scope of the invention as set forth in the following claims.

What is claimed is:

1. A method of assembling a meter for optically measuring analyte concentrations in a sample using at least one electro-optics component, the method comprising:
   providing a support surface having at least one contact pad formed thereon;
   mounting a template having a cut-out portion corresponding to the contact pad confronting the support surface such that the contact pad is at least partially accessible through the corresponding cut-out portion; and
   connecting the electro-optics component to the contact pad.

2. The method of claim 1, further comprising the step of mounting an optics block confronting the electro-optics component, the optics block comprising at least one light directing element for communicating light between the electro-optics component and the sample.

3. The method of claim 2, further comprising the step of mounting a strip holder confronting the optics block, the strip holder having a light transmissive portion and a first strip engaging portion.

4. The method of claim 3, further comprising the step of enclosing the support surface, template, and optics block in a housing, the housing having a second strip engaging portion.

5. The method of claim 1, wherein the support surface comprises a PCB.

6. The method of claim 2, wherein the step of mounting an optics block comprises attaching the optics block to the support surface.

7. The method of claim 6, wherein the step of mounting an optics block comprises heat staking the optics block to the support surface.

8. The method of claim 7, wherein the heat staking is effected using pins passing through the template.

9. The method of claim 1, wherein the template is aligned with the support surface using at least one boss provided on either one of the template or support surface, the boss engaging a corresponding hole provided on the other one of the template or support surface.

10. The method of claim 3, wherein the strip holder is aligned with the optics block using at least one pin provided on either one of the strip holder or optics block, the pin engaging a corresponding hole provided on the other one of the strip holder or optics block.

11. The method of claim 10, wherein the optics block is provided with tabs for prohibiting relative rotation between the strip holder and optics block.

12. The method of claim 3, wherein the sample is provided on a test strip, the first strip engaging portion positively locating the test strip on the strip holder in an engagement position.

13. The method of claim 12, wherein the test strip is provided with first and second pins, the first strip engaging portion comprising a hole for mating with the first pin and a keyway mating with the second pin.

14. The method of claim 3, wherein the light transmissive portion comprises an aperture through which light from the sample is communicated to the optics block.

15. The method of claim 4, wherein the sample is provided on a test strip, and wherein the second strip engaging portion comprises a tab for resiliently retaining the test strip against the strip holder.

16. The method of claim 1, wherein the cut-out portion comprises a pocket portion and a non-pocket portion, the step of connecting comprising sliding the electro-optic component in the plane of the template from the non-pocket portion to the pocket portion.

17. The method of claim 2, wherein the step of connecting comprises:

applying a conductive adhesive to the contact pad; and curing the conductive adhesive prior to mounting the optics block.

18. The method of claim 1, wherein the at least one electro-optics component comprises an LED and a pair of photodetectors.

19. The method of claim 12, wherein the strip holder operates to form a light-tight shield substantially preventing ambient light from reaching the electro-optics component in the engagement position.

20. A meter assembly for optically measuring sample analyte concentrations comprising:

a support surface having at least one contact pad formed thereon;

a template confronting the support surface and having cut-out portions corresponding to the contact pads; and at least one electro-optics component connected to a contact pad of the support surface and disposed in a corresponding cut-out portion.

21. The assembly of claim 20, further comprising an optics block confronting the electro-optics component and having at least one light directing element, the light directing element communicating light between the electro-optics element and the sample.

22. The assembly of claim 21, wherein the optics block is mounted to the support surface.

23. The assembly of claim 22, wherein the optics block is mounted to the support surface using pins passing through the template, the pins being heat staked to the support surface.

24. The assembly of claim 21, further comprising a strip holder having a light transmissive portion in optical alignment with the light directing element and a first strip engaging portion.

25. The assembly of claim 24, wherein the strip holder is mounted to the optics block using at least one pin and hole combination.

26. The assembly of claim 25, wherein the optics block is provided with tabs for preventing rotation of the strip holder.

27. The assembly of claim 24, further comprising a test strip adapted to contain the sample, the test strip being removably mountable to the strip holder in an engagement position and having an alignment portion for engagement with the engagement portion.

28. The assembly of claim 27, wherein the alignment portion comprises first and second pins, and wherein the engagement portion comprises a hole for mating with said first pin and a keyway for mating with said second pin.

29. The assembly of claim 27, further comprising a housing having a tab formed thereon, the tab resiliently biasing the test strip in the engagement position.

30. The assembly of claim 20, wherein the support surface comprises a PCB.

* * * * *